United States Patent
Davis

(10) Patent No.: US 8,960,201 B1
(45) Date of Patent: Feb. 24, 2015

(54) FOOT SCRUBBING DEVICE

(71) Applicant: Hazel M. Davis, Temple Terrace, FL (US)

(72) Inventor: Hazel M. Davis, Temple Terrace, FL (US)

(*) Notice: Subject to any disclaimer, the term of this patent is extended or adjusted under 35 U.S.C. 154(b) by 0 days.

(21) Appl. No.: 14/062,038

(22) Filed: Oct. 24, 2013

(51) Int. Cl.
- A45D 29/18 (2006.01)
- A45D 29/04 (2006.01)
- A61B 17/54 (2006.01)

(52) U.S. Cl.
CPC ............. *A61B 17/54* (2013.01); *A45D 29/04* (2013.01)
USPC ....................................... 132/76.4; 132/75.6

(58) Field of Classification Search
CPC ....... A45D 29/00; A45D 29/04; A45D 29/05; A45D 29/18; A45D 2029/045; A45D 29/06; A61B 17/54
USPC .............. 132/76.4, 200, 73, 73.5, 75.3, 75.6; 401/6–8; 15/104.16, 111, 229.11, 15/167.3, 229.13, 244.1; D28/56–59; 601/131, 135, 137; 451/523, 524, 533, 451/534
See application file for complete search history.

(56) References Cited

U.S. PATENT DOCUMENTS

| | | | | |
|---|---|---|---|---|
| 1,002,377 A * | 9/1911 | Ekenborg | | 30/27 |
| 2,055,219 A * | 9/1936 | Perrine | | 132/76.4 |
| D133,008 S * | 7/1942 | McCall | | D19/73 |
| 2,563,163 A * | 8/1951 | Exibard | | 132/76.4 |
| 2,774,983 A * | 12/1956 | Crowther | | 15/229.13 |
| 3,131,701 A * | 5/1964 | Emerson | | 132/76.4 |
| 3,196,885 A * | 7/1965 | Emerson | | 132/76.4 |
| 3,923,070 A * | 12/1975 | Tsukamoto | | 132/73 |
| 4,184,499 A * | 1/1980 | Seidler | | 132/75.6 |
| 4,246,914 A * | 1/1981 | Keyser | | 132/76.4 |
| 4,286,610 A * | 9/1981 | Jones et al. | | 132/76.4 |
| D276,276 S * | 11/1984 | Bankier | | D28/59 |
| 4,683,898 A * | 8/1987 | Lojovich | | 132/76.4 |
| 4,757,571 A * | 7/1988 | Young | | 15/167.3 |
| 5,088,509 A * | 2/1992 | Savage, III | | 132/76.5 |
| D345,627 S | 3/1994 | Thariani | | |
| D364,226 S * | 11/1995 | Hartmann | | D24/147 |
| 5,465,740 A * | 11/1995 | Kim | | 132/73.6 |
| 5,577,997 A | 11/1996 | Thariani et al. | | |
| 5,709,490 A | 1/1998 | Dyas | | |
| 5,732,719 A * | 3/1998 | Godbout | | 132/76.4 |
| 5,816,266 A * | 10/1998 | Cone | | 132/76.4 |
| 5,960,506 A | 10/1999 | Reuven | | |
| 5,996,590 A * | 12/1999 | Steege | | 132/76.4 |
| D430,357 S | 8/2000 | Nash et al. | | |
| D442,741 S * | 5/2001 | Rieser | | D28/59 |
| 6,640,812 B2 * | 11/2003 | Ayzman | | 132/76.4 |
| D483,910 S | 12/2003 | O'Brien, II | | |
| 6,913,025 B2 * | 7/2005 | Cho | | 132/76.4 |
| D530,859 S * | 10/2006 | Motta | | D28/59 |
| D563,048 S * | 2/2008 | Kim et al. | | D28/59 |
| D676,607 S * | 2/2013 | Park | | D28/59 |
| 2002/0193061 A1* | 12/2002 | Park | | 451/557 |
| 2005/0066988 A1* | 3/2005 | Park | | 132/76.4 |
| 2005/0081870 A1* | 4/2005 | Jancik | | 132/76.4 |
| 2006/0054177 A1* | 3/2006 | Kim | | 132/76.4 |

(Continued)

*Primary Examiner* — Vanitha Elgart

(57) ABSTRACT

A foot scrubbing device removes dead or callused skin from a foot. The device includes a handle and a planar panel coupled to and extending from a second end of the handle. The panel has a first face and a second face. A perimeter edge is coupled to and extends around the first face and the second face of the panel. A first abrasive surface is coupled to and covers the first face of the panel. A second abrasive surface is coupled to and covers the second face of the panel. The second abrasive surface has a grit size different than a grit size of the first abrasive surface.

11 Claims, 3 Drawing Sheets

(56) References Cited

U.S. PATENT DOCUMENTS

| | | | |
|---|---|---|---|
| 2007/0250079 A1* | 10/2007 | Kern | 606/131 |
| 2008/0223385 A1* | 9/2008 | Cha | 132/76.4 |
| 2010/0012139 A1 | 1/2010 | Perez | |
| 2010/0037906 A1* | 2/2010 | Ionis et al. | 132/76.5 |
| 2010/0145359 A1* | 6/2010 | Keller | 606/131 |
| 2011/0219561 A1 | 9/2011 | Tran | |

* cited by examiner

FOOT SCRUBBING DEVICE

BACKGROUND OF THE DISCLOSURE

Field of the Disclosure

The disclosure relates to scrubbing devices and more particularly pertains to a new scrubbing device for removing dead or callused skin from a foot.

SUMMARY OF THE DISCLOSURE

An embodiment of the disclosure meets the needs presented above by generally comprising a handle and a planar panel coupled to and extending from a second end of the handle. The panel has a first face and a second face. A perimeter edge is coupled to and extends around the first face and the second face of the panel. A first abrasive surface is coupled to and covers the first face of the panel. A second abrasive surface is coupled to and covers the second face of the panel. The second abrasive surface has a grit size different than a grit size of the first abrasive surface.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
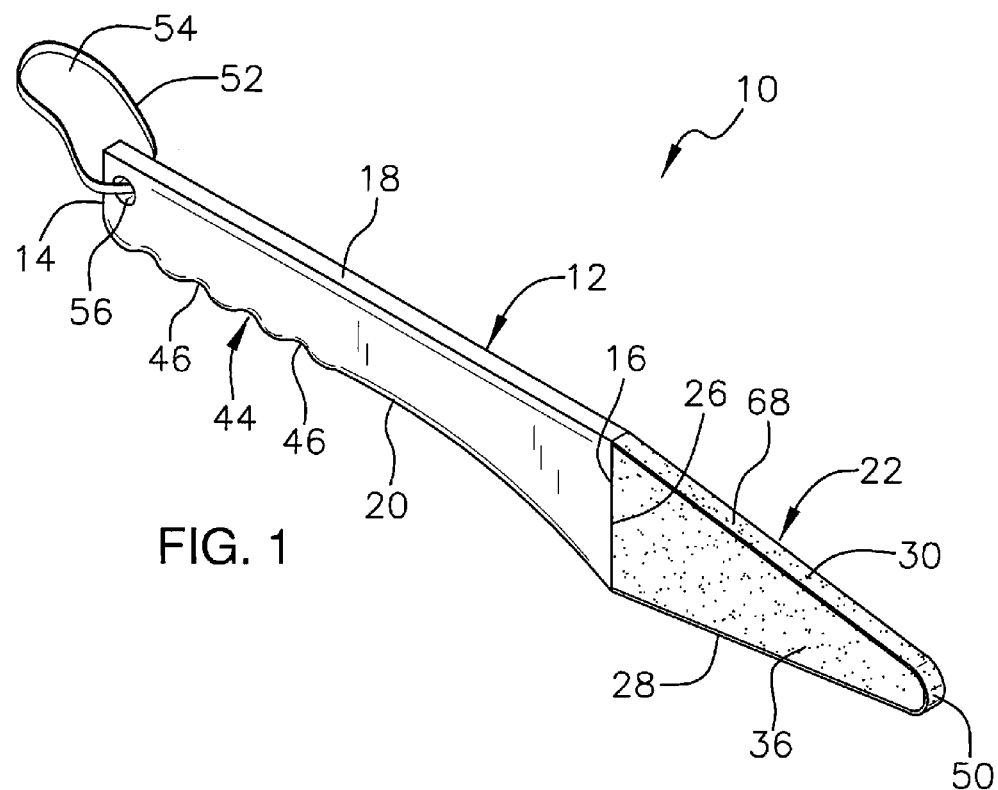
FIG. 1 is a top front side perspective view of a foot scrubbing device according to an embodiment of the disclosure.
Figure 2:
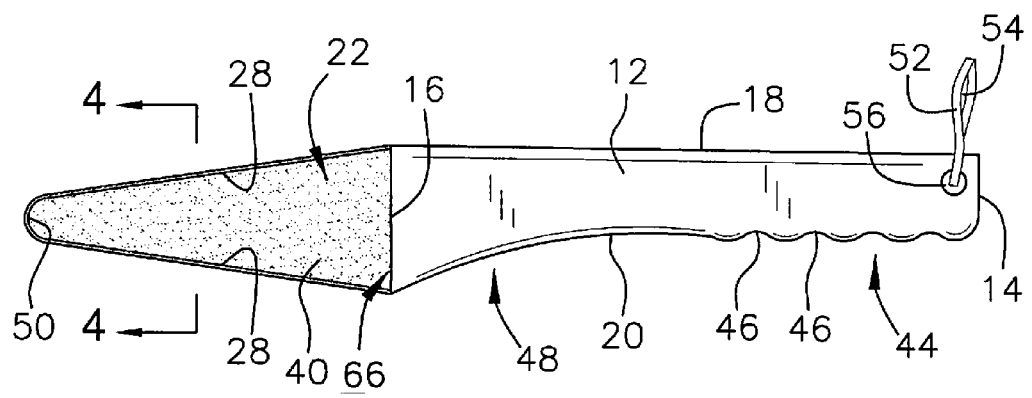
FIG. 2 is a side view of an embodiment of the disclosure.
Figure 3:
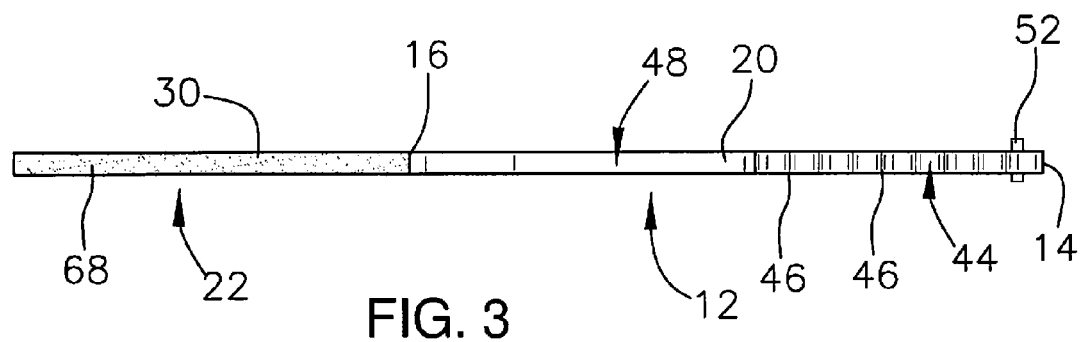
FIG. 3 is a bottom view of an embodiment of the disclosure.
Figure 4:
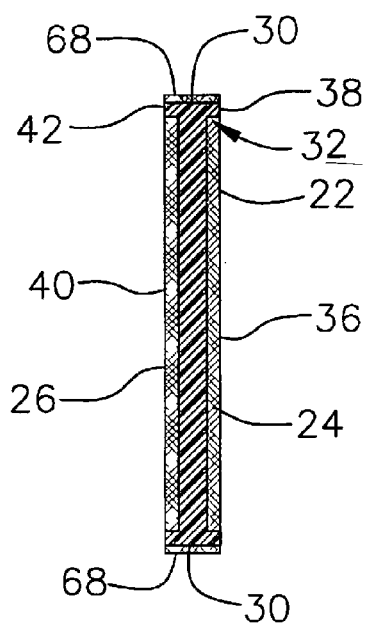
FIG. 4 is a cross-sectional view of an embodiment of the disclosure taken along line 4-4 of FIG. 2.
Figure 5:
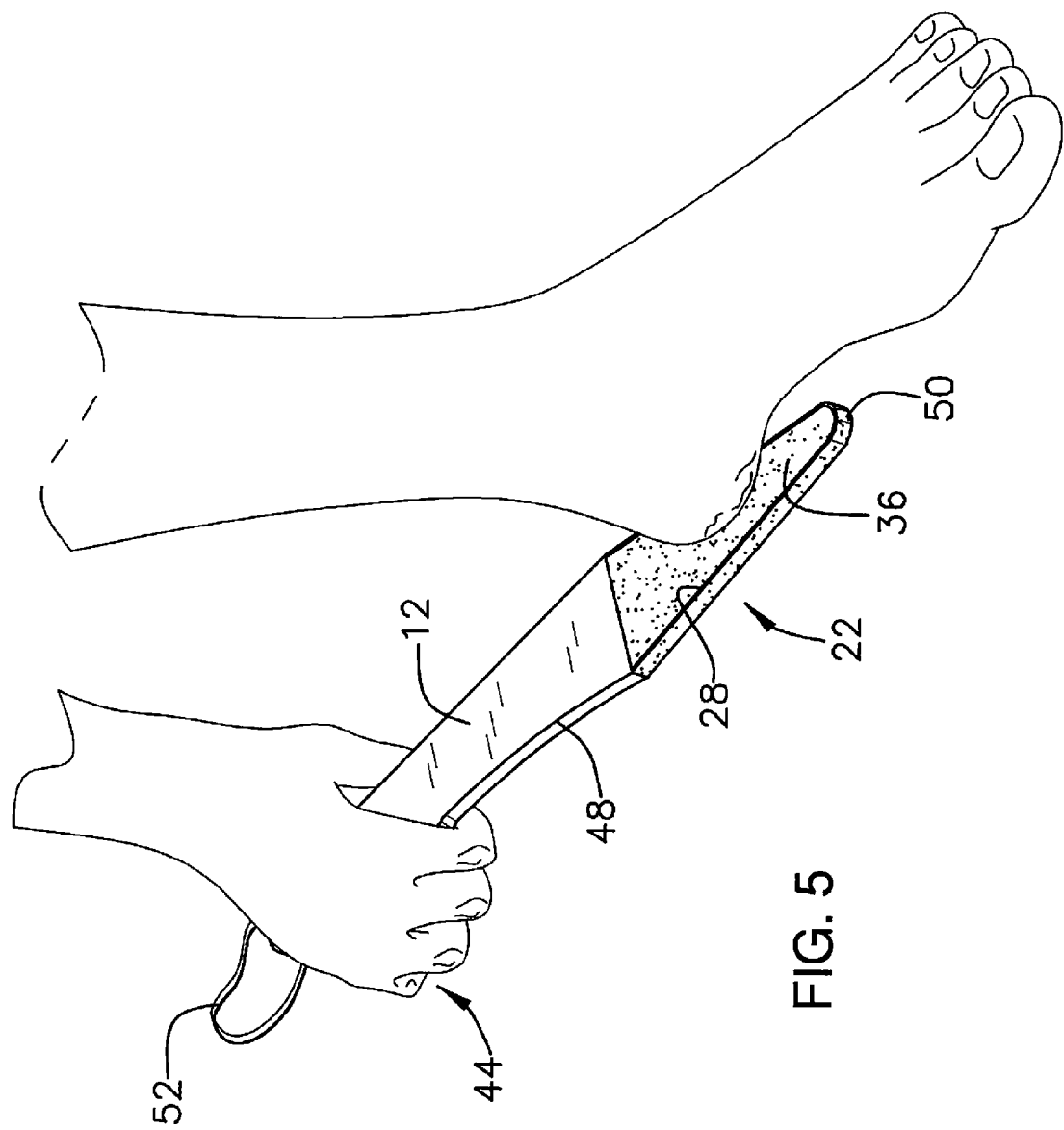
FIG. 5 is a perspective view of an embodiment of the disclosure in use.

With reference now to the drawings, and in particular to FIGS. 1 through 5 thereof, a new scrubbing device embodying the principles and concepts of an embodiment of the disclosure and generally designated by the reference numeral 10 will be described.

As best illustrated in FIGS. 1 through 5, the foot scrubbing device 10 generally comprises a handle 12 having a first end 14 and a second end 16. The handle 12 has a top edge 18 extending from the first end 14 to the second end 16. The handle 12 also has a bottom edge 20 extending from the first end 14 to the second end 16. A planar panel 22 is coupled to and extends from the second end 16 of the handle 12. The panel 22 has a first face 24 and a second face 26. The panel 22 may be substantially triangular having a base edge 66 adjacent to the second end 16 of the handle 12 and a pair of side edges 28 extending away from the handle 12 such that the panel 22 tapers extending away from the handle 12. A junction 50 of the side edges 28 of the panel 22 may be rounded. A perimeter edge 30 is coupled to and extends around the first face 24 and the second face 26 of the panel 22. The perimeter edge 30 my have a thickness greater than a thickness of the panel 22. The panel 22 may be coupled to the perimeter edge 30 in a medial section 32 of the perimeter edge 30 wherein the first face 24 and the second face 26 of the panel 22 are inset relative to the perimeter edge 30. The perimeter edge 30 may be covered by an abrasive 68 extending along lateral sides and around a junction to facilitate use of the perimeter edge between toes, fingers, or the like.

A first abrasive surface 36 is coupled to and covers the first face 24 of the panel 22. The first abrasive surface 36 may be substantially coplanar with a first outer face 38 of the perimeter edge 30. Similarly, a second abrasive surface 40 is coupled to and covers the second face 26 of the panel 22. The second abrasive surface 40 has a grit size different than a grit size of the first abrasive surface 36 such that each of the first abrasive surface 36 and the second abrasive surface 40 provides a unique amount of abrasion when scrubbed on skin. Thus, relatively fine and coarse abrasion is provided by the device 10 by selecting the desired one of the first abrasive surface 36 and the second abrasive surface 40 to scrub against the skin. The second abrasive surface 40 may also be substantially coplanar with a second outer face 42 of the perimeter edge 30.

A grip section 44 of the bottom edge 20 of the handle 12 defines a plurality of indentations 46 extending into the handle 12. The grip section 44 extends from the first end 14 of the handle 12 towards the second end 16 of the handle 12. An extension section 48 of the bottom edge 20 of the handle 12 defines a parabolic shape extending between the grip section 44 and the panel 22. A strap 52 may be coupled to the handle 12 forming a loop 54. An aperture 56 may extend through the handle 12 proximate the first end 14 of the handle 12. The strap 52 may extend through the aperture 56.

In use, the handle 12 is grasped using the grip section 44. Each of the first abrasive surface 36 and the second abrasive surface 40 may be used depending on the desired amount of abrasion to scrub against a foot to remove dead skin or calluses. The device 10 may be provided in a plurality of scaled sizes.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

I claim:
1. A foot scrubbing device comprising:
a handle having a first end and a second end, said handle having a top edge extending from said first end to said second end, said handle having a bottom edge extending from said first end to said second end;

a planar panel coupled to and extending from said second end of said handle, said panel having a first face and a second face;

a perimeter edge coupled to and extending around said first face and said second face of said panel;

a first abrasive surface coupled to and covering said first face of said panel;

a second abrasive surface coupled to and covering said second face of said panel, said second abrasive surface having a grit size different than a grit size of said first abrasive surface; and an abrasive extending along a pair of lateral sides of said perimeter edge and around a junction of said lateral sides of said perimeter edge.

2. The device of claim 1, further comprising a grip section of said bottom edge of said handle defining a plurality of indentations extending into said handle, said grip section extending from said first end of said handle towards said second end of said handle.

3. The device of claim 2, further comprising an extension section of said bottom edge of said handle defining a parabolic shape extending between said grip section and said panel.

4. The device of claim 1, further comprising said panel being substantially triangular having a base edge adjacent to said second end of said handle and a pair of side edges extending away from said handle wherein said panel tapers extending away from said handle.

5. The device of claim 4, further comprising a junction of said side edges of said panel being rounded.

6. The device of claim 1, further comprising said perimeter edge having a thickness greater than a thickness of said panel.

7. The device of claim 6, further comprising said panel being coupled to said perimeter edge in a medial section of said perimeter edge wherein said first face and said second face of said panel are inset relative to said perimeter edge.

8. The device of claim 1, further comprising a strap coupled to said handle.

9. The device of claim 8, further comprising an aperture extending through said handle proximate said first end of said handle, said strap extending through said aperture.

10. The device of claim 8, further comprising said strap forming a loop.

11. A foot scrubbing device comprising:

a handle having a first end and a second end, said handle having a top edge extending from said first end to said second end, said handle having a bottom edge extending from said first end to said second end, said handle being planar;

a planar panel coupled to and extending from said second end of said handle, said panel having a first face and a second face, said panel being substantially triangular having a base edge adjacent to said second end of said handle and a pair of side edges extending away from said handle wherein said panel tapers extending away from said handle, said planar panel being coplanar with said handle;

a perimeter edge coupled to and extending around said first face and said second face of said panel, said perimeter edge having a thickness greater than a thickness of said panel, said panel being coupled to said perimeter edge in a medial section of said perimeter edge wherein said first face and said second face of said panel are inset relative to said perimeter edge;

an abrasive extending along a pair of lateral sides of said perimeter edge and around a junction of said lateral sides of said perimeter edge;

a first abrasive surface coupled to and covering said first face of said panel said first abrasive surface being substantially coplanar with a first outer face of said perimeter edge;

a second abrasive surface coupled to and covering said second face of said panel, said second abrasive surface having a grit size different than a grit size of said first abrasive surface, said second abrasive surface being substantially coplanar with a second outer face of said perimeter edge;

a grip section of said bottom edge of said handle defining a plurality of indentations extending into said handle, said grip section extending from said first end of said handle towards said second end of said handle;

an extension section of said bottom edge of said handle defining a parabolic shape extending between said grip section and said panel;

a junction of said side edges of said panel being rounded;

a strap coupled to said handle, said strap forming a loop; and an aperture extending through said handle proximate said first end of said handle, said strap extending through said aperture.

* * * * *